United States Patent [19]

Dodds

[11] 4,001,423
[45] Jan. 4, 1977

[54] 2-(2-ETHOXY)ETHOXYETHYL BENZIMIDAZOLECARBAMATE

[76] Inventor: Dale I. Dodds, 560 S. Orange Grove Blvd., Pasadena, Calif. 91105

[22] Filed: June 20, 1975

[21] Appl. No.: 588,933

[52] U.S. Cl. .............................. 424/273; 260/309.2
[51] Int. Cl.[2] ................. A01N 9/22; C07D 235/12
[58] Field of Search ................. 424/273; 260/309.2

[56] References Cited
UNITED STATES PATENTS 3,657,443  4/1972  Klopping .......................... 424/273

OTHER PUBLICATIONS

1 Sims et al., "Phytopathological Notes", Nov. 1969, pp. 1775–1776.

*Primary Examiner*—V. D. Turner
*Attorney, Agent, or Firm*—Donald Diamond

[57] ABSTRACT

Phytotherapeutic compositions comprising diethylene glycol ether solutions of 2-(2-ethoxy)ethoxyethyl benzimidazolecarbamate are prepared by: (a) heating and agitating an opaque, fluid suspension of methyl 1-(butylcarbamoyl)-2-benzimidazolecarbamate and dimethylsulfoxide until the fluid clarifies whereby the butylcarbamoyl group is removed from the carbamate; (b) adding methanol to the clarified fluid to precipitate a paste containing methyl 2-benzimidazolecarbamate and methanol; (c) separating the supernatant fluid from the paste; and (d) admixing diethyleneglycol monoethyl ether with the paste to form a fluid slurry and heating the slurry, with agitation, until it clarifies to thereby obtain a diethylene glycol monoethyl ether solution of 2-(2-ethoxy)ethoxyethyl benzimidazolecarbamate, and thereafter diluting the solution with diethylene glycol monoethyl ether to obtain suitable use concentrations of the carbamate. The phytotherapeutic compositions are useful as an aid in the control of plant fungus disease.

5 Claims, No Drawings

2-(2-ETHOXY)ETHOXYETHYL BENZIMIDAZOLECARBAMATE

FIELD OF THE INVENTION

This invention relates to 2-(2-ethoxy)ethoxyethyl benzimidazolecarbamate, a method for preparing the same and the use thereof in the control of plant fungus disease.

PRIOR ART

In view of the destructive effect of pathogenic fungi on trees and other plants, there is a need for an effective systemic fungicide for controlling such fungi. A composition which has been found to have high toxicity and good residual protectant activity against a number of pathogenic fungi as well as a high level of plant safety is methyl 1-(butylcarbamoyl)-2-benzimidazolecarbamate. This composition, for which the generic name benomyl has been adopted and which has been described in U.S. Pat. No. 3,631,176 (Klopping, 1971), has the following structural formula:

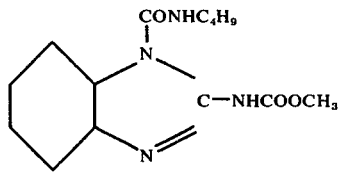

Although benomyl has shown a high degree of preventative and therapeutic activity against a wide range of pathogenic fungi, its practical application to trees and other plants has been limited because of its very low solubility characteristics in fluid carriers.

OBJECTS

An object of this invention is to provide a phytotherapeutic composition derived from benomyl which has the advantages of benomyl, namely, significant fungitoxicity with little or no phytotoxicity but which has substantially improved solubility characteristics in fluid carriers.

Another object of this invention is to provide a phytotherapeutic composition comprising 2-(2-ethoxy) ethoxyethyl benzimidazolecarbamate.

A further object of this invention is to provide a method for preparing 2-(2 ethoxy) ethoxyethyl benzimidazolecarbamate from benomyl.

A still further object of this invention is to provide a method for controlling plant fungus disease by treating plants with 2-(2-ethoxy) ethoxyethyl benzimidazolecarbamate.

SUMMARY OF THE INVENTION

This invention, in one aspect, is directed to phytotherapeutic compositions comprising 2-(2-ethoxy) ethoxyethyl benzimidazolecarbamate. In a second aspect, this invention is directed to a method for preparing 2-(2-ethoxy) ethoxyethyl benzimidazolecarbamate from benomyl which comprises heating an admixture of benomyl and dimethylsulfoxide, with agitation, until the fluid clarifies at a temperature between about 140° F and about 170° F; adding methanol to the clarified fluid, with cooling, to precipitate a paste comprising methyl 2-benzimidazolecarbamate and methanol; separating the supernatant fluid from the paste; and admixing the paste with diethylene glycol monoethyl ether and heating the admixture, with agitation, until the fluid clarifies at a temperature between 320° F and 330° F to obtain a diethylene glycol monoethyl ether solution of 2-(2-ethoxy) ethoxyethyl benzimidazolecarbamate. In a third aspect, the invention is directed to a method for controlling plant fungus disease which comprises treating plants with 2-(2-ethoxy) ethoxyethyl benzimidazolecarbamate.

DETAILED DESCRIPTION

The compositions of this invention comprise 2-(2-ethoxy) ethoxyethyl benzimidazolecarbamate which has the following structural formula:

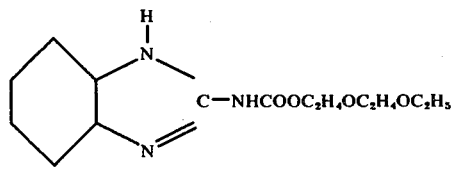

The aforesaid carbamate is advantageously dispensed in combination with a carrier wherein the carbamate is generally present in an amount from about 0.1 to about 2.5 percent by weight and, preferably, is present in an amount from about 0.5 to about 2.0 percent by weight, with the carrier being present in an amount to make up 100 percent by weight of the dispensed composition.

A suitable carrier which can be used in the preparation of stabilized solutions of the carbamate of this invention is diethylene glycol monoethyl ether.

The stabilized solutions of 2-(2-ethoxy) ethoxyethyl benzimidazolecarbamate can be prepared from benomyl, as a starting material. Benomyl is available as a formulated wettable powder under the registered trademark BENLATE which contains 50 percent, by weight, of benomyl.

In the initial step of the process, BENLATE is admixed with a polar solvent such as dimethylsulfoxide to form an opaque, fluid suspension and the fluid suspension is heated, with agitation, until the fluid clarifies at a temperature between about 140° F and 170° F. The amount of dimethylsulfoxide in the admixture is not critical and it is economically advantageous to only use that amount which is sufficient to form a suspension with benomyl. Typically, at least about 6 parts by weight of dimelthylsulfoxide are admixed with 1 part by weight of benomyl or, based on BENLATE, at least about 3 parts by weight of dimethylsulfoxide are admixed with 1 part by weight of BENLATE containing 50 weight percent benomyl. A practical upper limit is about 50 parts by weight of dimethylsulfoxide per 1 part by weight of benomyl. The initial heating step removes butylisocyanate from the benomyl molecule.

Methanol is added to the clarified fluid, with cooling, to precipitate a paste comprising methyl 2-benzimidazolecarbamate and methanol. The paste typically contains about 25 weight percent of the carbamate although the concentration thereof may range from about 20 to about 30 weight percent. The amount of methanol added to the clarified fluid is not critical and it is generally added in an amount corresponding to at least about the weight of the clarified fluid and, preferably, in an amount corresponding to at least about 2.5 times the weight of the clarified fluid with an upper practical limit being about 5 times the weight of such fluid. Following the addition of methanol to the clarified fluid, the rate of precipitation is enhanced by cooling the fluid to a temperature between about 32° F and 42° F. Thereafter, the supernatant fluid is removed from the paste by any suitable separation technique such as decantation.

The paste is then admixed with at least a sufficient amount of diethylene glycol monoethyl ether to form a fluid slurry which is heated, with agitation, until the fluid clarifies at a temperature between about 320° F and about 330° F to thereby obtain a diethylene glycol ethyl ether solution of 2-(2-ethoxy) ethoxyethyl benzimidazolecarbamate. Typically, at least about 4 parts by weight of diethylene glycol ethyl ether are admixed with 1 part by weight of the paste to form the fluid slurry. Although larger amounts of the glycol ether can be used, it is advantageous to use the minimum amount necessary to prepare a suitable slurry in order to reduce the heating time to clarification and thereby maximize yield of the ester interchange, reaction product and minimize decomposition of the feed carbamate, methyl 2-benzimidazolecarbamate. A practical upper limit for the glycol ether in this step of the process is about 10 parts by weight of the glycol ether per 1 part by weight of the paste.

To the glycol ether solution of 2-(2-ethoxy) ethoxyethyl benzimidazolecarbamate, there is added diethylene glycol monoethyl ether in an amount to provide a phytotherapeutic solution containing generally from about 0.1 to about 2.5 weight percent and, preferably, from about 0.5 to about 2.0 weight percent of 2-(2-ethoxy) ethoxyethyl 2-benzimidazolecarbamate.

The phytotherapeutic solutions prepared in accordance with the method of this invention are very stable and can be stored for an extended period of time without any significant precipitation or flocculation. The solutions can be applied to trees and other plants through stem injection, as a foliar spray or by soil treatment and are effective against a wide variety of pathogenic fungi. The solutions of the invention are particularly adapted for injection directly into the trunk of a tree as, for example, by the method described in U.S. Pat. No. 3,304,655. These solutions are advantageously introduced into the trees through Mauget pressurized capsules (4 ml.) which are connected to feeder tubes which are inserted into the trunks of the trees along a circumference thereof at 4 to 6 inch intervals.

The diethylene glycol ether solutions of 2-(2-ethoxyl) ethoxyethyl benzimidazolecarbamate can be used as an aid in the control of a wide variety of fungus disease affecting trees as, for example:

| Tree | Disease | Fungus |
| --- | --- | --- |
| Bishop Pine | Pitch Canker | Fusarium sp. |
| Swiss Stone Pine | Dieback | Leptographium lundbergii |
| Monterey Pine | Pitch Canker | Fusarium sp. |
| Horsechestnut | Stem Canker | Stagonospora sp. |
| S. Magnolia | Stem and Branch Canker | Phomopsis sp. |
| Black Oak | Wilt | Chalara sp. |
| Mimosa | Wilt | Fusarium perniciosum |
| Portugal Laurel | Wilt | Fusarium oxysporum f. pruni |
| Live Oak | Wilt | Verticillium albo-atrum |
| Camphor Tree | Wilt | Verticilium albo-atrum |
| Calif. White Oak | Oak Decline | Clitocybe oleracearum and Verticillium albo-atrum |
| Sycamore | Canker Stain | Ceratocystit fimbriata |
| Hankow Willow | Dothiorella Wilt | Dothiorella sp. |
| Santa Barbara Ceonothus | Wilt Complex | Fusarium oxysporum and Armillaria mellea |
| Fruitless Mulberry | Ceratocystis Canker | Ceratocystis fimbriata |
| Deodar Cedar | Twig and Branch Canker | Periconiella sp. |

The following example further illustrates the invention.

EXAMPLE I

To a vessel containing 40 grams of BENLATE (50% by weight of benomyl), there was added, with agitation, 120 ml. of dimethylsulfoxide to form an opaque, fluid suspension and the fluid suspension was heated, with agitation, until it clarified at a temperature of about 160° F. This heating step converted benomyl to methyl 2-benzimidazolecarbamate with butyl isocyanate being released in gaseous form.

500 ml. of methanol were added to the clarified fluid which was then cooled at a temperature of about 35° F for about 18 hours to obtain a paste-like precipitate. The supernatant fluid was decanted from the paste. The paste, which weighed 36.5 grams, contained about 9.5 grams (about 25 wt. %) of methyl 2-benzimidazolecarbamate and about 27 grams (about 75 wt. %) of methanol.

218 grams of diethylene glycol monoethyl ether were added to the paste, with agitation, to form a fluid slurry which was heated, with agitation, until the fluid clarified at a temperature between 320° and 330° F. During the heating step, the paste gradually dissolved with the evolution of gases. There was obtained a diethylene glycol ether solution of 2-(2-ethoxy) ethoxyethyl benzimidazolecarbamate. To this solution, there was added 610 grams of diethylene glycol monoethyl ether to obtain 837 grams of a phytotherapeutic solution containing 14.2 grams (1.7 wt. %) of 2-(2-ethoxy) ethoxyethyl 2-benzimidazolecarbamate.

The analytical data for 2-(2-ethoxy) ethoxyethyl benzimidazolecarbamate is as follows: Elemental analysis for C, H, N gave 57.5% C; 6.82% H; and 14.47% N; the corresponding values for $C_{14}H_{19}N_3O_4$ are 57.33% C; 6.52% H; and 14.33% N. NMR ($CDCl_3$) analysis showed 4 protons, 10 protons for the $-CO-OCH_2CH_2-OCH_2CH_2-OCH_2$ group, 3 protons for the $-CH_3$ group on the end of the oxyethylene chain, and 2 exchangeable protons. Thus, the analysis shows that the butylcarbamoyl group has been removed from benomyl, and that the methyl carbamate group has undergone transesterification with diethylene glycol monoethyl ether. The mass spectrum (MS) shows a molecular ion at m/e 293 and major fragments at m/e 191, 159, 131, 104, 59 and 45.

Other ingredients which can be advantageously combined with the phytotherapeutic compositions of this invention include antibiotics, metal chelates, systemic insecticides, sugars, other fungicides, growth regulants and the like.

That which is claimed is:

1. 2-(2-ethoxy)ethoxyethyl benzimidazolecarbamate.

2. A fungitoxic composition comprising from about 0.1 to about 2.5 percent by weight of 2-(2-ethoxy) ethoxyethyl benzimidazolecarbamate and a carrier therefor to make up 100 percent by weight of the composition.

3. A composition according to claim 2 wherein the carrier is diethylene glycol monoethyl ether.

4. A composition according to claim 3 wherein the carbamate is present in an amount from about 0.5 to about 2.0 percent by weight.

5. A method for preparing a diethylene glycol monoethyl ether solution of 2-(2-ethoxy)ethoxyethyl benzimidazolecarbamate, which comprises:

admixing methyl 1-(butylcarbamoyl)-2-benzimidazolecarbamate with at least a sufficient amount of dimethylsulfoxide to form an opaque, fluid suspension and heating said opaque, fluid suspension, with agitation, until the fluid clarifies at a temperature between about 140° and 170° F;

adding methanol to said clarified fluid, with cooling, to precipitate a paste comprising methyl 2-benzimidazolecarbamate and methanol;

separating the supernatant fluid from said paste; and admixing said paste with at least a sufficient amount of diethylene glycol monoethyl ether to form a fluid slurry and heating said fluid slurry, with agitation, until the fluid clarifies at a temperature between about 320° F and 330° F to obtain a diethylene glycol monoethyl ether solution of 2-(2-ethoxy) ethoxyethylbenzimidazolecarbamate.

* * * * *